(12) United States Patent
Proksa et al.

(10) Patent No.: US 11,116,465 B2
(45) Date of Patent: Sep. 14, 2021

(54) DARK-FIELD ENHANCED VIRTUAL X-RAY COLONOSCOPY

(71) Applicants: KONINKLIJKE PHILIPS N.V., Eindhoven (NL); TECHNISCHE UNIVERSITAET MUENCHEN, Munich (DE)

(72) Inventors: Roland Proksa, Neu Wulmstorf (DE); Alexander André Fingerle, Munich (DE); Daniela Muenzel, Munich (DE); Franz Josef Pfeiffer, Unterfohring (DE); Thomas Koehler, Norderstedt (DE); Peter Benjamin Theodor Noel, Unterfohring (DE); Maximilian Von Teuffenbach, Munich (DE); Julia Herzen, Munich (DE); Konstantin Willer, Munich (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 294 days.

(21) Appl. No.: 15/756,602

(22) PCT Filed: Sep. 1, 2016

(86) PCT No.: PCT/IB2016/055216
§ 371 (c)(1),
(2) Date: Mar. 1, 2018

(87) PCT Pub. No.: WO2017/046670
PCT Pub. Date: Mar. 23, 2017

(65) Prior Publication Data
US 2018/0289350 A1    Oct. 11, 2018

Related U.S. Application Data

(60) Provisional application No. 62/219,163, filed on Sep. 16, 2015.

(51) Int. Cl.
*A61B 6/00* (2006.01)
*A61B 6/03* (2006.01)

(52) U.S. Cl.
CPC ............ *A61B 6/5217* (2013.01); *A61B 6/032* (2013.01); *A61B 6/463* (2013.01); *A61B 6/466* (2013.01);
(Continued)

(58) Field of Classification Search
CPC .............................. A61B 6/481; A61B 6/484
See application file for complete search history.

(56) References Cited

U.S. PATENT DOCUMENTS 7,889,838 B2   2/2011   David
7,983,381 B2   7/2011   David
(Continued)

OTHER PUBLICATIONS

Velroyen et al, Microbubbles as a scattering contrast agent for grating-based x-ray dark-field imaging, Feb. 1, 2013, IOP Publishing, Physics in Medicine and Biology, 58, N37-N46 (Year: 2013).*
(Continued)

*Primary Examiner* — Rochelle D Turchen
(74) *Attorney, Agent, or Firm* — Larry Liberchuk

(57) ABSTRACT

A method of a virtual X-ray colonoscopy includes scanning (204) a dark-field contrast (144) insufflated colon lumen (140) with an X-ray scanner (110) configured for dark-field-contrast, which generates dark-field-contrasted projection data and attenuation projection data. The dark-field-contrasted projection data and the attenuation projection data are reconstructed (206) into one or more dark-field-contrasted images (148).

19 Claims, 2 Drawing Sheets

(52) U.S. Cl.
CPC .............. *A61B 6/481* (2013.01); *A61B 6/484* (2013.01); *A61B 6/50* (2013.01); *A61B 6/482* (2013.01)

(56) References Cited

U.S. PATENT DOCUMENTS

| | | | |
|---|---|---|---|
| 8,009,796 | B2 | 8/2011 | Popescu |
| 2005/0129169 | A1 | 6/2005 | Donnelly |
| 2006/0235296 | A1 | 10/2006 | Mattiuzzi |
| 2008/0055308 | A1* | 3/2008 | Dekel ..................... G06T 15/08 345/421 |
| 2011/0142316 | A1* | 6/2011 | Wang ................... G06T 11/006 382/131 |
| 2011/0293064 | A1 | 12/2011 | Huang |
| 2012/0243658 | A1 | 9/2012 | Geller |

OTHER PUBLICATIONS

Kuekle et al, Contrast-Enhanced Dark Lumen PET/CT and MR Colonography in a Rodent Polyp Model: Initial Results with Histopathologic Correlation, Oct. 2005, AJR:185, 1045-1047 (Year: 2005).*
Velroyen et al, Grating-based X-ray Dark-field Computed Tomography of Living Mice, Aug. 13, 2015, Elsevier, EBioMedicine 2, 1500-1506 (Year: 2015).*
Herzen et al, Imaging Liver Lesions Using Grating-Based Phase-Contrast Computed Tomography with Bi-Lateral Filter Post-Processing, Jan. 2014, PLOS ONE, vol. 9, 1-9 (Year: 2014).*
Pfeiffer et al, Grating-based X-ray phase contrast for biomedical imaging applications, Feb. 5, 2013, Z. Med. Phys. 23(2013), 176-185 (Year: 2013).*
Tapfer, Small Animal X-ray Phase-Contrast Imaging, Jul. 2013, Technische Universitat Munchen, pp. 1-119 (Year: 2013).*
Rubin, et al., "Virtual colonoscopy: A novel imaging modality for colorectal cancer", Current Oncology Reports, vol. 3, No. 2, Mar. 1, 2001.
Pfeiffer, et al., "Hard-X-ray dark-field imaging using a grating interferometer", Nature Materials, vol. 7, No. 2, Feb. 1, 2008.
Velroyen, et al., "Note; Microbubbles as a scattering contrast agent for grating-based x-ray dark-field imaging"; Physics in Medicine and Biology, vol. 58, No. 4, Feb. 1, 2013.
Scherer, et al., "Non-invasive Differentiation of Kidney Stone Types using X-ray Dark-Field Radiography"; Scientific Reports, 2014.
Arfelli, et al., "Microbubbles as x-ray scattering contrast agents using analyzer-based imaging"; Phys. Med. Biol. 55 (2010) 1643-1658.
Michel, et al., "On a dark-field signal generated by micrometer-sized calcifications in phase-contrast mammography"; Phys. Med. Biol. 58 (2013) 2713-2732.
Bech, et al., "Quantitative x-ray dark-field computed tomography" Phys. Med. Biol. 55 (2010) 5529-5539.
Yashiro, et al., "On the origin of visibility contrast in x-ray Talbot interferometry"; Aug. 2, 2010 / vol. 18, No. 16 / Optics Express.
Pfeiffer F. et al., "Grating-Based X-Ray Phase Contrast for Biomedical Imaging Applications", Medical Physics, vol. 23, issue 3, pp. 176-185, Sep. 2013.

* cited by examiner

DARK-FIELD ENHANCED VIRTUAL X-RAY COLONOSCOPY

CROSS REFERENCE TO RELATED APPLICATIONS

This application is the U.S. National Phase application under 35 U.S.C. § 371 of International Application No. PCT/IB2016/055216, filed Sep. 1, 2016, published as WO 2017/046670 on Mar. 23, 2017, which claims the benefit of U.S. Provisional Patent Application No. 62/219,163 filed Sep. 16, 2015. These applications are hereby incorporated by reference herein.

FIELD OF THE INVENTION

The following generally relates to x-ray medical imaging and cancer screening with specific application to computed tomography (CT) medical imaging and screening for colon polyps.

BACKGROUND OF THE INVENTION

Colonoscopies are typically done to patients for early identification of cancers and colon polyps, which can be a precursor to colon cancer. Polyps are small fingerlike protrusions of vascularized colon tissue that protrude from the colon wall into the colon lumen.

A typical colonoscopy is performed after cleansing the colon of stool or fecal material, which is usually performed by oral administration of a laxative with copious fluids done by the patient. During the colonoscopy procedure, the patient is typically given a sedative, and the colon is insufflated with air to maximize visibility. For example, the colon is naturally convoluted with folds, which makes inspection of the wall difficult to follow through the folds. By insufflation, the folds are opened and the wall of the colon more easily followed and inspected. An endoscope is inserted into the colon through the anus, and the endoscope includes a camera from which the healthcare practitioner can view the colon wall. Usually, a first visual inspection is done as the endoscope is inserted, and then a second visual inspection in closer detail is done for 25-30 minutes as the endoscope is withdrawn from the colon lumen, which can still sometimes miss polyps. Procedures that include the insertion of any instrument inside the patient involve risk to the patient. For example, one risk is the perforation of the colon wall by the endoscope.

Virtual colonoscopies are an alternative to avoid such risk and can be completed in shorter times involving the patient using low dose radiation. A detailed review can be done after the imaging process is completed. Virtual colonoscopy is the medical imaging of the colon and screening for polyps using an image, such as a CT image. However, one of limitations of a virtual colonoscopy has been that even though the colon is cleansed by the patient, not all fecal material is removed. Small pieces of fecal matter or residual stool can adhere in the convoluted intestinal wall, which may give a false positive appearance of a polyp. For example, the residual stool can include similar attenuation properties as colon tissue, which makes it difficult to distinguish based on the CT image. Another issue is delineating the polyps, which can be measured in millimeters, from folds in the intestinal wall and/or lumen.

In conventional CT imaging, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, in cases where different forms of tissue with similar absorption cross-sections are under investigation (e.g., different aspects of colon tissue, colon lumen, residual stool), the X-ray absorption contrast is relatively poor.

SUMMARY OF THE INVENTION

Aspects described herein address the above-referenced problems and others.

The following describes a virtual colonoscopy using a CT scanner configured for dark-field imaging, and a colon insufflated with dark-field contrast that contrast a lumen of the colon in the dark-field contrast imaging. Intravenous contrast can be used to contrast colon tissue to further distinguish polyps.

In one aspect, a method of a virtual X-ray colonoscopy includes scanning a dark-field contrast insufflated colon lumen with an X-ray scanner configured for dark-field-contrast, which generates dark-field-contrasted projection data and attenuation projection data. The dark-field-contrasted projection data and the attenuation projection data are reconstructed into one or more dark-field-contrasted images.

In another aspect, a virtual computed x-ray colonoscopy system includes an X-ray scanner, and a reconstructor. The X-ray scanner is configured to generate dark-field-contrasted projection data and attenuation projection data of a colon lumen filled with a fluid of dark-field contrast. The reconstructor is configured to reconstruct the dark-field-contrasted projection data and the attenuation projection data into one or more dark-field-contrasted images.

In another aspect, a method of a virtual computed tomography (CT) colonoscopy includes scanning a dark-field contrast insufflated colon lumen and intravenous contrasted vascularized colon tissue with a CT scanner configured for dark-field-contrast, which generates dark-field-contrasted projection data and contrast enhanced attenuation projection data. The dark-field-contrasted projection data and the contrast enhanced attenuation projection data are reconstructed into one or more dark-field-contrasted images. Polyps in the one or more dark-field-contrasted images are identified based on the dark-field contrasted colon lumen and the attenuation contrasted colon tissue.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
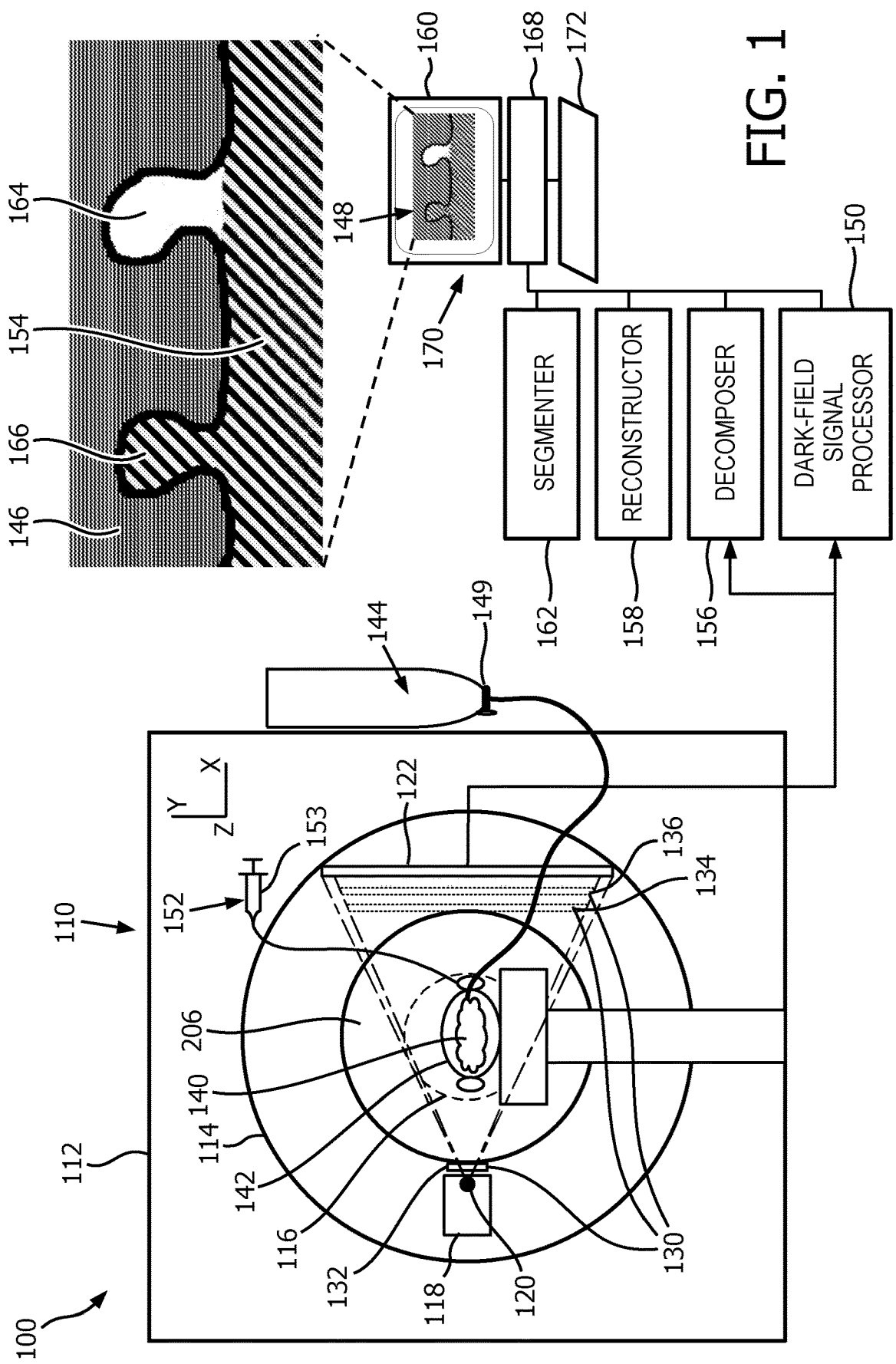
FIG. 1 schematically illustrates an embodiment of a dark-field enhanced virtual X-ray colonoscopy system.

Initially referring to FIG. 1, an embodiment of a dark-field enhanced virtual X-ray colonoscopy system 100 is schematically illustrated. The system includes an X-ray scanner 110, such as a CT scanner, a radiographic scanner, and the like, which is configured to imaging at least dark-field or scatter, and attenuation of a patient. In one embodiment, a CT scanner is configured for multi-contrast imaging, which includes grating-based Dark-field CT (DFCT), e.g. scatter contrast, with conventional CT, e.g. attenuation contrast. The CT scanner includes a generally stationary gantry 112, which houses a rotating gantry 114 that is rotatably supported by the stationary gantry 112 and rotates around an examination region 116 about a z-axis. A radiation source 118 (e.g., an X-ray tube) with a focal spot 120 is rotatably supported by the rotating gantry 114, rotates with the rotating gantry 114, and emits radiation that traverse the examination region 116. The radiation source 118 is configured to emit single or multiple energy spectra of x-ray radiation. For example, the radiation source generates a single spectrum. In another example, the radiation source generates two spectra, e.g. dual source or spectral imaging.

A radiation sensitive detector array 122 is located opposite the radiation source 118 across the examination region 116. The radiation sensitive detector array 122 detects radiation traversing the examination region 116 and generates a signal indicative thereof. In one embodiment, the radiation sensitive detector array 122 includes multiple layers, which detect radiation at different energies. The detected radiation includes signal intensities with an attenuation component, a phase-contrast component, and a dark-field component.

An X-ray imaging interferometer 130 is also rotatably supported by the rotating gantry 114 and rotates with the rotating gantry 114. The X-ray imaging interferometer 130 includes three grating structures, a source grating 132, a phase grating 134 and an analyzer grating 136. The X-ray interferometer 130 is adapted to provide dark-field contrast through the examination region 116 to the detector 122. An example of a CT enhanced with the X-ray imaging interferometer is described in application Ser. No. 13/514,682, filed Jun. 8, 2012, entitled "Phase Contrast Imaging," and assigned to Koninklijke Philips Electronics N. V., the entirety of which is incorporated herein by reference. The detected radiation includes corresponding positions of the analyzer grating 136. In a conventional phase stepping approach tissue of the patient according to the attenuation component has the effect of reducing or attenuating the detected signal intensity. The phase-contrast component has the effect of shifting the position of the detected signal intensity. The dark-field component has the effect of modulating a depth of the detected signal intensity. Other approaches besides the phase stepping are contemplated in deriving the attenuation component and the dark-field component from the detected radiation using the interferometer 130.

An endo-rectal contrast fluid of dark-field contrast 144 insufflates a colon 140 of a patient 142, which expands and/or unfolds a lumen 146 of the colon 140 and provides dark-field contrast within the lumen 146 in a volumetric image 148 of the lumen and surrounding colon tissue. For example, the colon of the patient is filled with air filled serum albumin shells held in a tank insufflated through the rectum using a delivery device 149, such as a nozzle inserted into the anus and connected to a container. The dark-field contrast 144 causes slight refraction of coherent x-rays or scatter. The dark-field contrast 144 includes small hollow particles with a shell and a core, and the shell refracts very differently from the core. For example, the dark-field contrast 144 can include air, inert gas, or perfluorocarbon cores. The shells can be made of a lipid, a protein or a polymer. An example of a spherical particle is a sonographic contrast agent known as microbubbles. The shells of the dark-field contrast can be spherical with diameters between 1-1000 microns. During imaging, the detector array 122 generates an intensity signal and includes a corresponding position of the analyzer grating 136, which are processed by a dark-field signal processor 150 to generate projection data with dark-field contrast. The generated projection data includes the attenuation component and the dark-field component (and the phase-contrast component).

The patient can be injected intravenously with an intravenous (IV) contrast 152, such as iodine, gadolinium, and the like using an injection device 153. The IV contrast 152 contrasts colon tissue 154 through vascularization in the volumetric image 148. With the attenuation signal component of the patient with the IV contrast 152, the decomposer 156 can decompose projection data into the contrast enhanced projection data. With the attenuation signal of the patient without the intravenous contrast, the decomposer 156 generates attenuation projection data, e.g. non-contrast enhanced. In one embodiment, the decomposer 156 can decompose the IV contrast 152 with the x-ray scanner 110 configured for spectral imaging according to spectral imaging techniques known in the art. The decomposition can separate the IV contrast 152 either as projection data or image data.

A reconstructor 158 reconstructs the generated dark-field projection data and the attenuation projection data into the volumetric dark-field and attenuation images 148. The volumetric images 148 can be displayed as two dimensional (2D) views on a display device 160 or stored in a storage system such as a Picture Archiving and Communication System (PACS), Radiology Information System (RIS), Electronic Medical Record (EMR), and the like. In one embodiment, the dark-field projection data and the attenuation projection data are separately reconstructed. In another embodiment, the dark-field projection data and the attenuation projection data are combined and reconstructed as a single image. In another embodiment, the reconstructed dark-field image and the reconstructed attenuation image are combined as a single image. For example, information from one image can be differently encoded in the combined image, such as with color and/or patterns known in the art. For example, the brightness of a pixel is defined by attenuation values, and the color is defined by the dark-field pixel value. Reconstruction can include registration either as slices or as a volume. The volumetric image 148 can include the colon tissue 154 contrasted with the IV contrast 152.

In DFCT imaging, the interferometer 130 is energy dependent on the emitted spectra. High angular sensitivity of the interferometer 130 provides small radiation phase-shifts, which can also generate phase wrapping at small deflection angles. Phase wrapping leads to strong artifacts in the reconstructed dark-field images. In one embodiment, dual energy or spectral imaging can be used to estimate the unwrapped phase shift. For example, using a maximum likelihood estimation technique with an energy sensitive detector and modelled energy dependencies, the wrapped phase shift can be unwrapped. Other spectral imaging techniques such as dual-source CT, kVp-switching, dual layer detection or photon counting detection with energy discrimination can be utilized to improve the IV contrast delineation and used to improve the dark-field processing such as phase wrapping.

A segmenter 162 can segment the colon lumen 146 using segmentation techniques known in the art based on the lumen structure and/or contrast. The segmenter 162 can segment the contrasted colon tissue 154. In some embodiment, the residual stool 164 appears as non-dark-field contrasted, non-intravenous contrasted attenuated image data.

In some embodiments, polyps 166 can be identified visually as protrusions into the colon lumen 146 of the expanded and/or unfolded colon tissue 154 differentiated from the non-dark-field contrasted, non-intravenous contrasted residual stool 164 visually. In another embodiment, the segmenter 162 can identified using automated segmentation algorithms known in the art to identify the polyps 166 based on structure and/or vascularization. For example, the segmented colon lumen 146 indicates polyps 166 that project into the colon lumen 146, e.g. as a negative projection or depression in the colon lumen 146. In another embodiment, the segmenter and/or reconstructor removes the dark-field contrasted lumen from the volumetric image 148.

The dark-field signal processor 150, the decomposer 156, the reconstructor 158 and the segmenter 162 comprise one or more processors 168 (e.g., a microprocessor, a central processing unit, digital processor, and the like) configured to execute at least one computer readable instruction stored in a computer readable storage medium, which excludes transitory medium and includes physical memory and/or other non-transitory medium. The processor 168 may also execute one or more computer readable instructions carried by a carrier wave, a signal or other transitory medium. The processor 168 can include local memory and/or distributed memory. The processor 168 can include hardware/software for wired and/or wireless communications. For example, the lines indicate communications paths between the various components which can be wired or wireless. The processor 168 can comprise a computing device 170, such as a desktop computer, a server, a laptop, a mobile device, a body worn device, distributed devices, combinations and the like. The computing device includes one or more input devices 172, such as a keyboard, mouse, microphone, touch screen, and the like. The input devices 172 can provide for input of imaging parameters and/or display views of the reconstructed volumetric dark-field contrast image 148.

Figure 2:
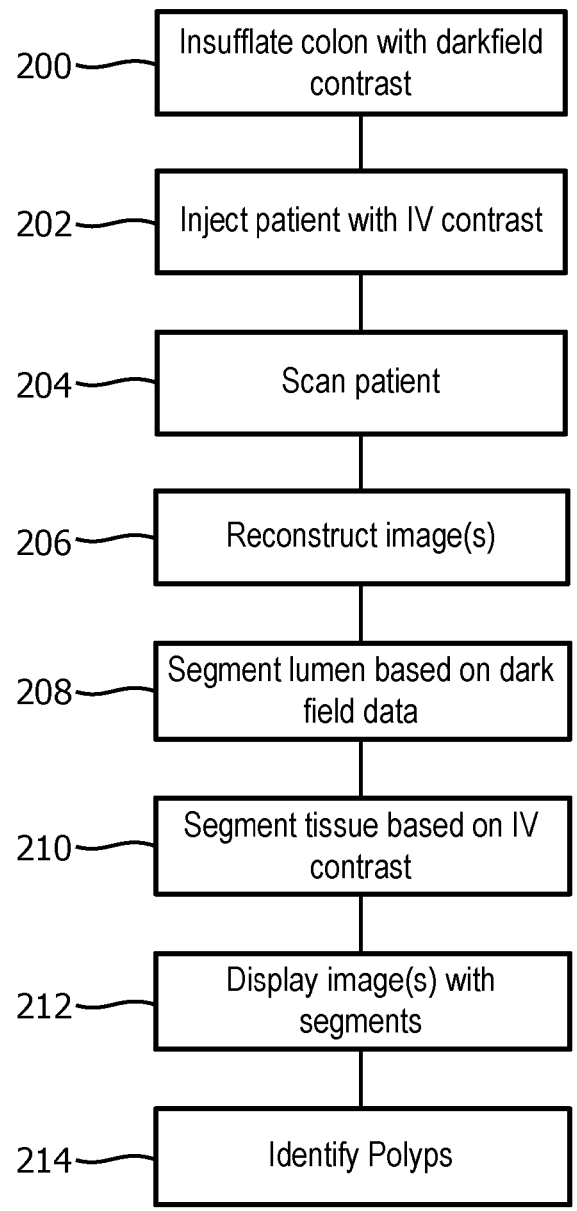
FIG. 2 illustrates an embodiment of a method of dark-field enhanced virtual X-ray colonoscopy.

With reference to FIG. 2, an embodiment of a method of dark-field enhance virtual x-ray colonoscopy is flowcharted. At 200, a cleansed colon lumen 140 of a patient 142 is insufflated with an endo-rectal contrast fluid of the dark-field contrast 144, which expands and/or unfolds the cleansed colon lumen 140. At 202, the patient can be injected intravenously with a contrast agent 152, which contrasts vascularized tissue of the colon.

At 204, the patient is scanned with a x-ray scanner 110 configured for dark-field contrast imaging, which contrasts the dark-field contrast in the colon lumen. Projection data is generated, which include a dark-field contrasted component and an attenuation component. In one embodiment, the attenuation imaging generates contrast enhanced attenuation projection data of the IV contrast 152. In one embodiment, the x-ray scanner 110 is configured for spectral imaging and the attenuation imaging generates decomposed attenuation projection data based on the IV contrast 152.

At 206, the generated dark-field contrasted projection data and the attenuation contrasted projection data are reconstructed into one or more volumetric images 148. In one embodiment, the volumetric images 148 include the IV contrasted vascularized colon tissue 154. The reconstruction can include registration between the dark-field contrasted projection and the attenuation contrasted projection or the dark-field contrasted image data and the attenuation contrasted image data. The reconstruction with spectral imaging can include unwrapping the phase wrapping in the dark-field contrasted projection data, which can correct phase wrapping artifacts in the dark-field contrasted image.

At 208, the colon lumen 146 can be segmented in the volumetric dark-field contrasted images 148 based on the dark-field contrast 144. At 210, the colon tissue 154 in the volumetric images 148 can be segmented based on the IV contrast 152. In one embodiment, segmentation includes automatic identified of polyps 166 based on structure and/or vascularization. For example, colon tissue 154 can be identified based on structure from the reconstructed attenuation projection data and/or contrast enhanced reconstructed attenuation projection data. The unfolded colon lumen 146 dark-field contrasted can also be used to separate the colon lumen from colon tissue 154 including polyps 166 and/or residual stool 164 based on structure and dark-field contrast.

The reconstructed image(s) 148, the segmented colon lumen 146, and/or the segmented colon tissue 154 can be displayed in one or more views on the display device 160 and/or stored in a computer memory, such as a Picture Archiving and Communication System (PACS), Hospital Information System (HIS), departmental Radiology Information System (RIS), and the like. The segmented structures and/or the identified polyps can be differentiated in the display with color, patterns, brightness, combinations and the like. Polyps 166 can be identified in the displayed image manually or through automated methods based on structure and contrasted lumen and tissues.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of a virtual X-ray colonoscopy, the method comprising:
   scanning a dark-field contrast insufflated colon lumen with an X-ray scanner configured for dark-field-contrast, which generates dark-field-contrasted projection data and attenuation projection data, wherein the attenuation projection data includes an intravenous contrast which contrasts vascularized colon tissue in the attenuation projection data;
   reconstructing the dark-field-contrasted projection data and the attenuation projection data into one or more dark-field-contrasted images;
   identifying an imaged colon lumen and imaged colon tissue in the one or more dark-field-contrasted images based on the dark-field contrast from the reconstructed dark-field-contrasted images and/or reconstructed attenuation projection data; and
   identifying polyps based on the imaged colon lumen as a negative projection or depression in the imaged colon lumen of the imaged colon tissues.

2. The method according to claim 1, wherein the scanning includes computed tomography (CT) dual energy or spectral scanning.

3. The method according to claim 1, further including:
   segmenting an imaged colon lumen in the one or more dark-field-contrasted images based on the dark-field contrast.

4. The method according to claim 1, further including:
segmenting imaged colon tissue in the one or more dark-field-contrasted images based on the intravenous contrast.

5. The method according to claim 1, further including:
displaying on a display at least one of the one or more dark-field-contrasted images, a segmented colon lumen, and a segmented colon tissue.

6. The method according to claim 1, wherein the dark-field contrast includes spherical particles between 1-1000 microns in diameter.

7. The method according to claim 1, wherein the dark-field contrast includes a shell formed from at least one of a lipid, a protein or a polymer, and filled with at least one of air, an inert gas, and a perfluorocarbon.

8. A virtual computed x-ray colonoscopy system, the system comprising:
an x-ray scanner configured to generate dark-field-contrasted projection data and attenuation projection data of a colon lumen filled with a fluid of dark-field contrast;
an injection device for injecting an intravenous contrast that contrasts a vascularized colon tissue in the attenuation projection data;
processing circuitry configured to:
reconstruct the dark-field-contrasted projection data and the attenuation projection data into one or more dark-field-contrasted images;
identify an imaged lumen and imaged colon tissue in the one or more dark-field-contrasted images based on the dark-field contrast from the reconstructed dark-field-contrasted images and/or reconstructed attenuation projection data; and
identify polyps based on the imaged colon lumen a negative projection or depression in the imaged colon lumen of the imaged colon tissue.

9. The system according to claim 8, wherein the X-ray scanner is configured for computed tomography (CT) spectral imaging.

10. The system according to claim 8, wherein the processing circuitry is configured to segment at least one an imaged colon lumen in the one or more dark-field-contrasted images based on the dark-field contrast or segment imaged colon tissue in the one or more dark-field-contrasted images based on the intravenous contrast.

11. The system according to claim 8, further including:
a display configured to display at least one of the one or more dark-field-contrasted images, a segmented colon lumen, and a segmented colon tissue.

12. The system according to claim 8, wherein the processing circuitry is configured to identify polyps based on structure and contrast.

13. The system according to claim 8, wherein the dark-field contrast includes spherical particles between 1-1000 microns in diameter.

14. The system according to claim 8, wherein the dark-field contrast includes a shell formed from at least one of a lipid, a protein, and a polymer.

15. The system according to claim 8, wherein the dark-field contrast includes particles filled with at least one of air, an inert gas, and a perfluorocarbon.

16. The method according to claim 1, wherein the polyps are identified as contrasted protrusions into the colon lumen of an expanded and/or unfolded colon tissue and/or using an automated segmentation algorithm configured to identify the polyps based on a structure and/or vascularization.

17. The method according to claim 1, wherein the reconstructing comprises unwrapping a phase wrapping in the dark-field contrasted projection data.

18. The method according to claim 17, wherein the unwrapping corrects phase wrapping artifacts in the dark-field contrasted image.

19. The method according to claim 16, the unfolded colon lumen dark-field contrasted is used to separate the colon lumen from the colon tissue including the polyps and/or a residual stool based on the structure and the dark-field contrast.

* * * * *